(12) United States Patent
Fath et al.

(10) Patent No.: US 9,149,390 B2
(45) Date of Patent: Oct. 6, 2015

(54) DEVICE FOR APPLYING A MARKING TO THE HUMAN EYE

(75) Inventors: Hartmut Fath, Wiesloch (DE); Tobias Neuhann, Munich (DE)

(73) Assignee: Geuder AG, Heidelberg (DE)

( * ) Notice: Subject to any disclaimer, the term of this patent is extended or adjusted under 35 U.S.C. 154(b) by 252 days.

(21) Appl. No.: 13/575,546

(22) PCT Filed: Nov. 23, 2010

(86) PCT No.: PCT/DE2010/001357
§ 371 (c)(1),
(2), (4) Date: Oct. 29, 2012

(87) PCT Pub. No.: WO2011/091777
PCT Pub. Date: Aug. 4, 2011

(65) Prior Publication Data
US 2013/0035705 A1     Feb. 7, 2013

(30) Foreign Application Priority Data

Jan. 27, 2010 (DE) .................. 10 2010 006 009
Jul. 13, 2010 (DE) .................. 10 2010 027 051
Sep. 8, 2010 (DE) .................. 10 2010 044 764

(51) Int. Cl.
*A61F 9/00* (2006.01)
*A61F 9/013* (2006.01)
*A61B 17/00* (2006.01)
*A61B 19/00* (2006.01)

(52) U.S. Cl.
CPC ..... *A61F 9/0136* (2013.01); *A61B 2017/00477* (2013.01); *A61B 2019/545* (2013.01); *A61B 2019/5408* (2013.01)

(58) Field of Classification Search
CPC ................. A61F 9/0136; A61B 2017/00477; A61B 2019/545; A61B 2019/5408
USPC ................. 606/166, 116, 107; 623/6.12
See application file for complete search history.

(56) References Cited

U.S. PATENT DOCUMENTS

| 4,417,579 | A | * | 11/1983 | Soloviev et al. | 606/166 |
| 4,515,157 | A | * | 5/1985 | Fedorov et al. | 606/166 |
| 4,705,035 | A | * | 11/1987 | Givens | 606/166 |
| 4,739,761 | A | * | 4/1988 | Grandon | 606/166 |

(Continued)

FOREIGN PATENT DOCUMENTS

DE      202008004593     6/2008

OTHER PUBLICATIONS

Translation of Written Opinion for Application No. PCT/DE2010/001357 dated Aug. 3, 2012.

(Continued)

*Primary Examiner* — Tuan V Nguyen
*Assistant Examiner* — Chima Igboko
(74) *Attorney, Agent, or Firm* — Alston & Bird LLP

(57) ABSTRACT

The invention relates to a device for applying a marking to the human eye, in particular on the cornea, comprising a marking head (1) and a retaining device (2) that supports the marking head (1), wherein the marking head (1) comprises a marking element (4) and a support that retains the marking element (4) in a specifiable or changeable angular position, wherein the support is arranged in a rotationally fixed manner relative to the retaining device (2) or a reference line and wherein the marking head (1) can be detached from the retaining device (2).

13 Claims, 6 Drawing Sheets

(56) References Cited

U.S. PATENT DOCUMENTS

| | | | |
|---|---|---|---|
| 4,744,362 A * | 5/1988 | Grundler | 606/166 |
| 4,961,744 A * | 10/1990 | Kilmer et al. | 606/166 |
| 5,006,123 A * | 4/1991 | Soll et al. | 606/166 |
| 5,226,905 A | 7/1993 | Hanna | |
| 5,314,439 A * | 5/1994 | Sugita | 606/166 |
| 5,368,604 A * | 11/1994 | Kilmer et al. | 606/166 |
| 5,395,385 A * | 3/1995 | Kilmer et al. | 606/166 |
| 5,938,674 A * | 8/1999 | Terry | 606/166 |
| 6,217,584 B1 * | 4/2001 | Nun | 606/107 |
| 6,217,596 B1 * | 4/2001 | Farah | 606/166 |
| 6,872,202 B2 * | 3/2005 | Gerlach et al. | 606/10 |
| 2002/0133145 A1 * | 9/2002 | Gerlach et al. | 606/4 |
| 2004/0143246 A1 * | 7/2004 | Maeda et al. | 606/5 |
| 2004/0167540 A1 * | 8/2004 | Gerten | 606/116 |
| 2005/0203554 A1 * | 9/2005 | Dykes | 606/166 |
| 2006/0287662 A1 * | 12/2006 | Berry et al. | 606/166 |
| 2006/0287663 A1 * | 12/2006 | Gayheart et al. | 606/166 |
| 2008/0228210 A1 * | 9/2008 | Davis | 606/166 |
| 2008/0300581 A1 * | 12/2008 | Wiechmann et al. | 606/4 |
| 2009/0254108 A1 * | 10/2009 | Davis | 606/166 |
| 2009/0318911 A1 * | 12/2009 | Kaushal et al. | 606/13 |

OTHER PUBLICATIONS

International Search Report for Application No. PCT/DE2010/001357 dated May 23, 2011.

International Preliminary Report on Patentability for Application PCT/DE2010/001357 dated Aug. 7, 2012.

* cited by examiner

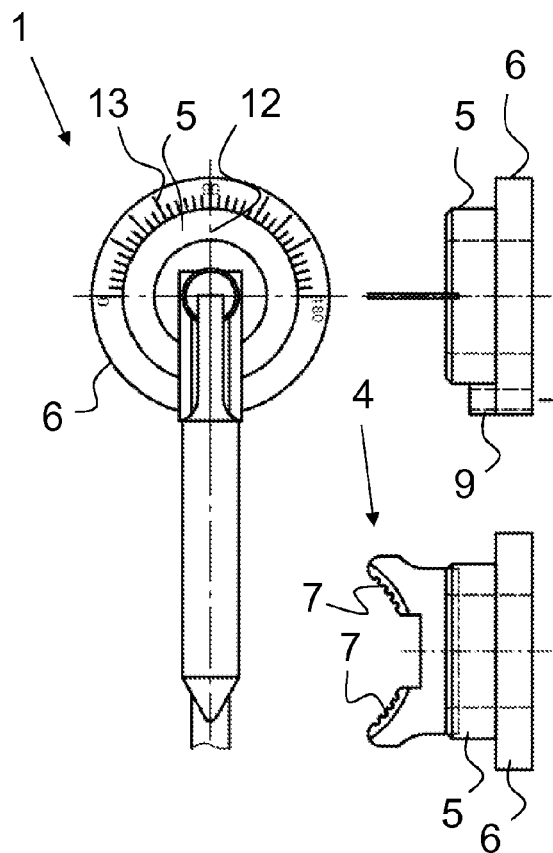
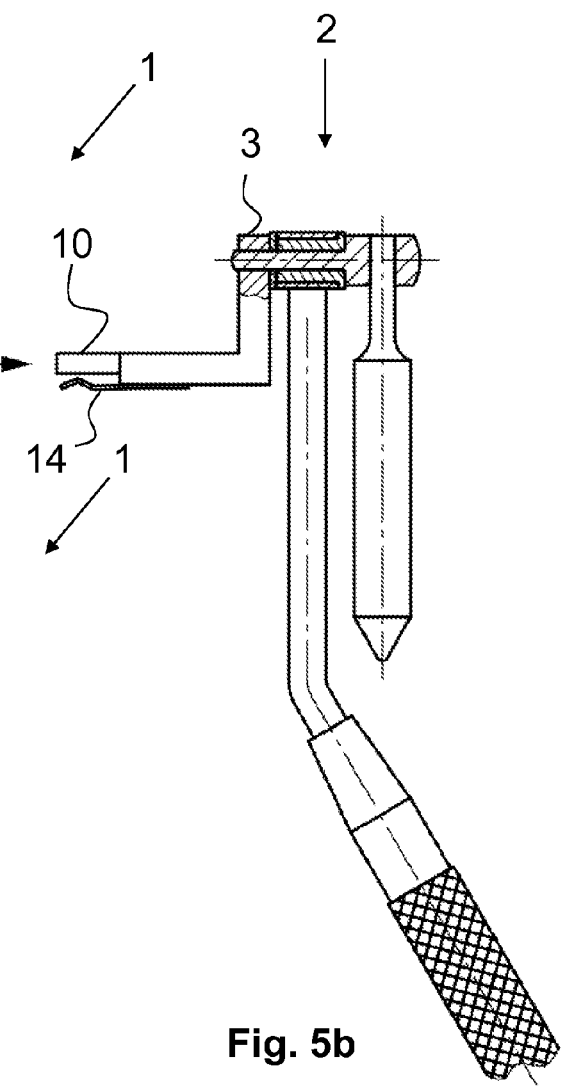
Fig. 5a
Fig. 5b

DEVICE FOR APPLYING A MARKING TO THE HUMAN EYE

CROSS-REFERENCE TO RELATED APPLICATIONS

This application is a national stage application filed under 35 U.S.C. 371 of International Application No. PCT/DE2010/001357, filed Nov. 23, 2010, which claims priority from German Patent Application No. 10 2010 044 764.1, filed Sep. 8, 2010, German Patent Application No. 10 2010 027 051.2, filed Jul. 13, 2010, and German Patent Application No. 10 2010 006 009.7, filed Jan. 27, 2010, each of which is incorporated by reference herein in its entirety.

BACKGROUND OF THE INVENTION

1. Field of the Invention

The invention relates to a device for applying a marking to the human eye, in particular to the cornea.

There is a need in principle for marking the cornea of the human eye, namely in preparation for ophthalmological intervention for correction of astigmatism, preferably for fixing a lens accurately on the iris.

2. Description of Related Art

Generic devices are already known in the art, generally under the designation "marking instrument".

A generic marking instrument is known from DE 20 2008 004 593 U1, in which this instrument serves to generate markings for ophthalmological surgery. The known instrument comprises a marking head which is pivotably connected to an instrument handle. A marking element provided on the instrument head is disposed so as to be adjustable in its angular position relative to a vertical weight, so that markings can be produced with an angular setting relative to the vertical.

The known generic device is exclusively in a hand-held surgical instrument. The marking head is firmly connected to the instrument. Because of the fixed co-ordination of the marking head with the instrument handle, the production of a marking is limited to the application of the specific instrument. Moreover there is always—inevitably—a relationship to the vertical, according to the selected setting. Moreover, the setting of the angular position of the marking element provided there is complex, and necessitates a separate tool, wherein for the setting the entire instrument should be positioned on a holding block.

The object of the present invention is to configure and to modify a device for applying a marking to the human eye, in particular to the cornea of the human eye, in such a way that with the simplest design it can be set simply in the angular position to discontinue and can be used both in conjunction with hand-held instruments and in conjunction with conventional devices from the field of ophthalmology.

SUMMARY OF VARIOUS EMBODIMENTS

This object is achieved according to the invention by the features of the various embodiments described herein. Accordingly the device according to the invention comprises a marking head and a retaining device which supports the marking head. The marking head is equipped with a marking element and a support which retains the marking element in a predeterminable or variable angular position. The support is non-rotatably disposed relative to the retaining device or a reference line, wherein the marking head can be detached from the retaining device.

According to the invention it has been recognised that it is extremely advantageous if the marking head is a component which can be manipulated independently and can be co-ordinated with any retaining device. In this case it is essential that the marking head supports the marking element which serves for marking the cornea, wherein the angular position of the marking head and thus of the marking element relative to a retaining device or a reference line is adjustable. In other words, the marking head is rotatable relative to the retaining device and can be detached therefrom or replaced.

In an advantageous manner the marking element comprises a marking tool which can be wetted by marking ink, preferably for marking a straight line or at least two points or sections of a straight line. By means of ink applied there a marking can be applied to the cornea, for example by means of water-soluble colour or ink.

In a particularly advantageous manner the marking tool which serves for marking consists of two serrated, preferably at least partially bent marking flanks which are pressed against the cornea of the eye. The colour which serves for marking should be applied beforehand to the surface of the marking tool. This may be done with a kind of stamp pad, a sponge or the like containing the colour.

For a particularly simple change to the angular position of the marking element or of the marking tool belonging thereto, the marking element is fastened on or in an inner rotating ring, wherein the rotating ring is rotatable in the support designed as an outer retaining ring—by hand or by means of a tool. Although the use of a tool could simplify the adjustment, the marking element or the inner rotating ring with the marking tool could be simply moved or rotated by hand, namely in the outer retaining ring.

It is also conceivable that the adjustment takes place before coupling of the marking head onto the retaining device, so that it is conceivable to rotate the inner rotating ring with a finger or by engagement in the inner passage of the rotating ring. In any case the angle setting can be carried out effortlessly with the marking head uncoupled.

In a further advantageous manner the inner rotating ring comprises a marker which symbolizes the angular position. The outer retaining ring may be equipped with a scale to indicate the angular position, preferably in the range from 0 to 180 degrees. Likewise a contrary arrangement or co-ordination of marker and scale is conceivable. In any case it is essential that the combination of inner rotating ring and outer retaining ring ensure a structurally simple adjustability, ideally actuated by hand, and independently of a retaining device which supports the marking head.

For coupling of the marking head to any retaining device, the marking head comprises special coupling means, namely for direct or indirect connection to the retaining device. In particular the coupling means are designed for a connecting piece to be inserted and received, wherein the connecting piece is co-ordinated with the retaining device or an interposed adapter.

In a particularly advantageous manner the coupling means and/or the connecting piece can be latched reciprocally, wherein the latching means which serve for this purpose are preferably spring-loaded. A secure coupling is possible in this way, regardless of the specific retaining device. Only the coupling means or receptacles and connecting pieces which are tailored to one another are essential.

In a particularly advantageous embodiment the retaining device is a conventional ophthalmological device, but without the actual functional head. Instead of this the marking head will be connected to the device. Stated more precisely, the retaining device may be a so-called slit lamp or a tonometer which is used in any case in ophthalmology. For connection of the marking head special coupling means are necessary in order to create a secure operative connection between the actual tonometer or the slit lamp and the marking head. The coupling means or the connecting piece should be adapted at the equipment end to the ophthalmological device. In terms of function, coupling means should be provided in the form of a special connecting piece to which the marking head can be securely connected. It is also conceivable that the marking head is equipped on the connection side with special coupling means which can be coupled directly to the slit lamp or to corresponding devices/housing parts of the slit lamp.

Alternatively it is conceivable that the same marking head with its coupling means can be connected—via an adapter or directly—to a hand-held ophthalmological instrument, wherein the hand-held ophthalmological instrument may preferably be an instrument with a gravity-loading pendulum mount which aligns with the horizontal or vertical. Here too the coupling ability and correspondingly the replaceability of the marking head plays a quite special role in order for example to be able—as required—to use marking heads with differently defined marking tools.

The ease of uncoupling of the marking head in this case also ensures convenient handling in the adjustability of the angular position of the marking tool.

Moreover it may be noted that the removability of the marking head favours handling thereof during cleaning.

Within the context of an alternative embodiment of the device according to the invention a direct coupling to a slit lamp can be achieved, and then the marking head can be coupled to the slit lamp without the adapter. Accordingly the marking element comprises an integral insertion zone for direct coupling to a retaining device or to the slit lamp.

BRIEF DESCRIPTION OF THE SEVERAL VIEWS OF THE DRAWINGS

There are now various possibilities for configuring and modifying the teaching of the present invention in an advantageous manner. In this connection reference is made on the one hand to the various embodiments described herein and on the other hand to the following explanation of two preferred embodiments of the invention with the aid of the drawings. In conjunction with the explanation of the preferred embodiments of the invention with reference to the drawings, preferred embodiments and modifications of the teaching are also explained in general. In the drawings:

FIGS. 5a, 5b show schematic partial views of the subject of FIG. 4, wherein the retaining device is an ophthalmological hand-held instrument.

DETAILED DESCRIPTION

Figure 1:
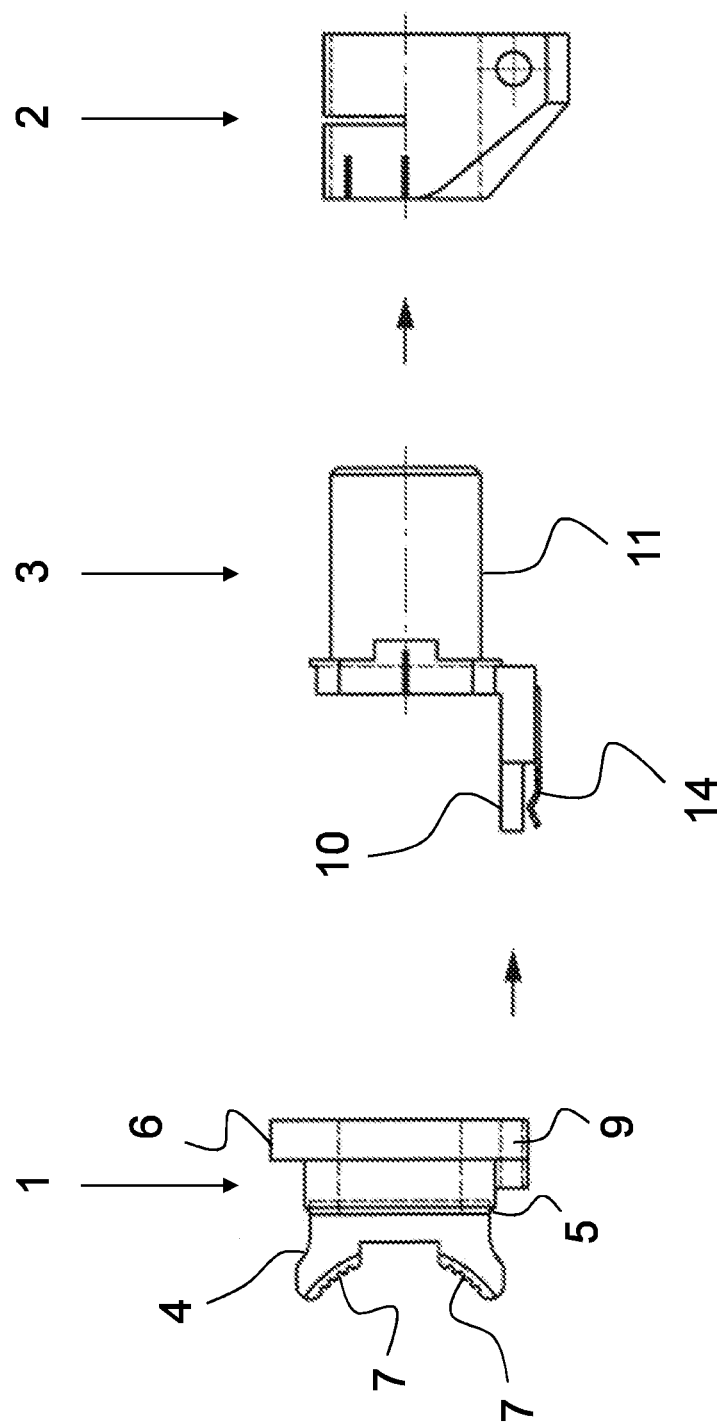
FIG. 1 shows a schematic view of a marking head for coupling to a component of a slit lamp with an adapter interposed.

FIG. 1 shows a schematic view of the individual components of a device for applying a marking to the human eye, namely to the cornea.

The device comprises a marking head 1 and a retaining device 2 which supports the marking head 1, wherein the retaining device is a component of a conventional slit lamp or a tonometer.

The coupling of the marking head 1 to the retaining element 2 takes place via coupling means 3 in the form of a adapter.

The marking head 1 is equipped with a marking element 4 which is fastened on an inner rotating ring 5 is. The inner rotating ring 5 is rotatable relative to an outer retaining ring 6, wherein the two rings—inner rotating ring 5 and outer retaining ring 6—are rotatable against one another.

Furthermore it can be seen from FIG. 1 that the marking element 4 of the marking head 1 is equipped with two claws 7 with serrated marking flanks. Moreover the marking head 1 comprises a receptacle 9 for introduction or insertion of a connecting piece 10 which is an integral component of the adapter 3. Thus a secure operative connection can be produced between the marking head 1 and the adapter 3. The adapter 3 comprises an insertion zone 11 which can be inserted into the part of the slit lamp which symbolizes the retaining device 2. Thus it is possible to connect the marking head 1 in a simple manner to a conventional slit lamp and to use the entire device for marking the cornea of the human eye, similar to the use of a conventional slit lamp or a tonometer.

FIGS. 2a, 2b and 2c show the adapter 3 inserted into the retaining device, wherein the connecting piece 10 serves for insertion into the receptacle 9 of the marking head 1. The receptacle 9 may be designed as a metal sleeve or as a corresponding hollow section.

FIG. 2a clearly shows the marking head 1, consisting of the inner rotating ring 5 with marker 12 and the outer retaining ring 6 with a scale 13 defining the angle setting. The scale 13 comprises a graduation from 0 to 180 degrees, so that any angle settings of the marking element 4 or of the claws 7 defining the marking tool are possible.

Furthermore, FIGS. 2a, 2b and 2c show clearly that the connecting piece 10 is designed as a profile which can be inserted into the receptacle 9, wherein the connecting piece 10 comprises a spring clip 14 for latching or securing the connection between the adapter 3 and the marking head 11.

The essential parts of the marking head 1 can be made of plastic. The marking element 4 or the claws 7 are advantageously made of metal. The same applies to the receptacle 9 of the marking head 1. Also the connecting piece 10 of the adapter 3 should be made of metal, preferably aluminium or stainless steel. The adapter 3 otherwise be a component made substantially from plastic.

Figure 2:
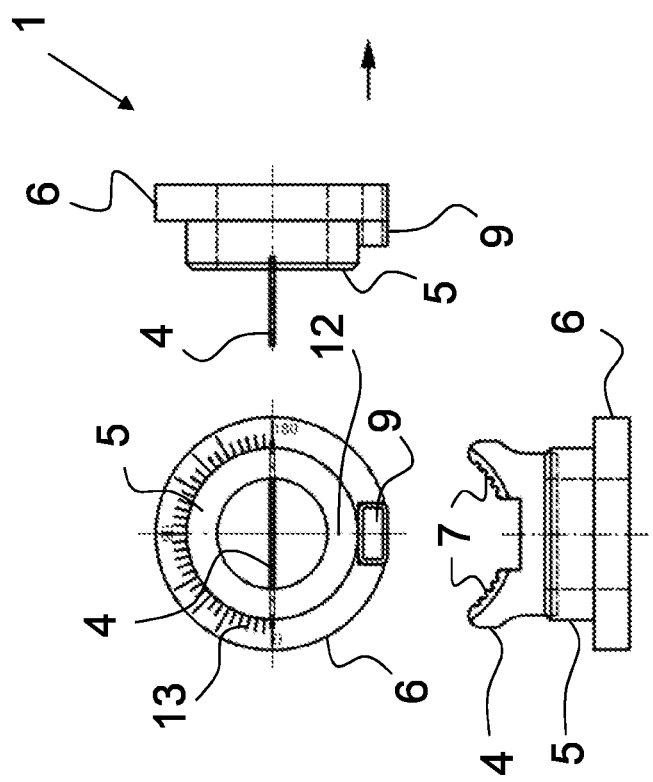
FIGS. 2a, 2b, 2c show schematic partial views of the subject of FIG. 1, wherein the ophthalmological component is a part of a slit lamp.
Figure 3:
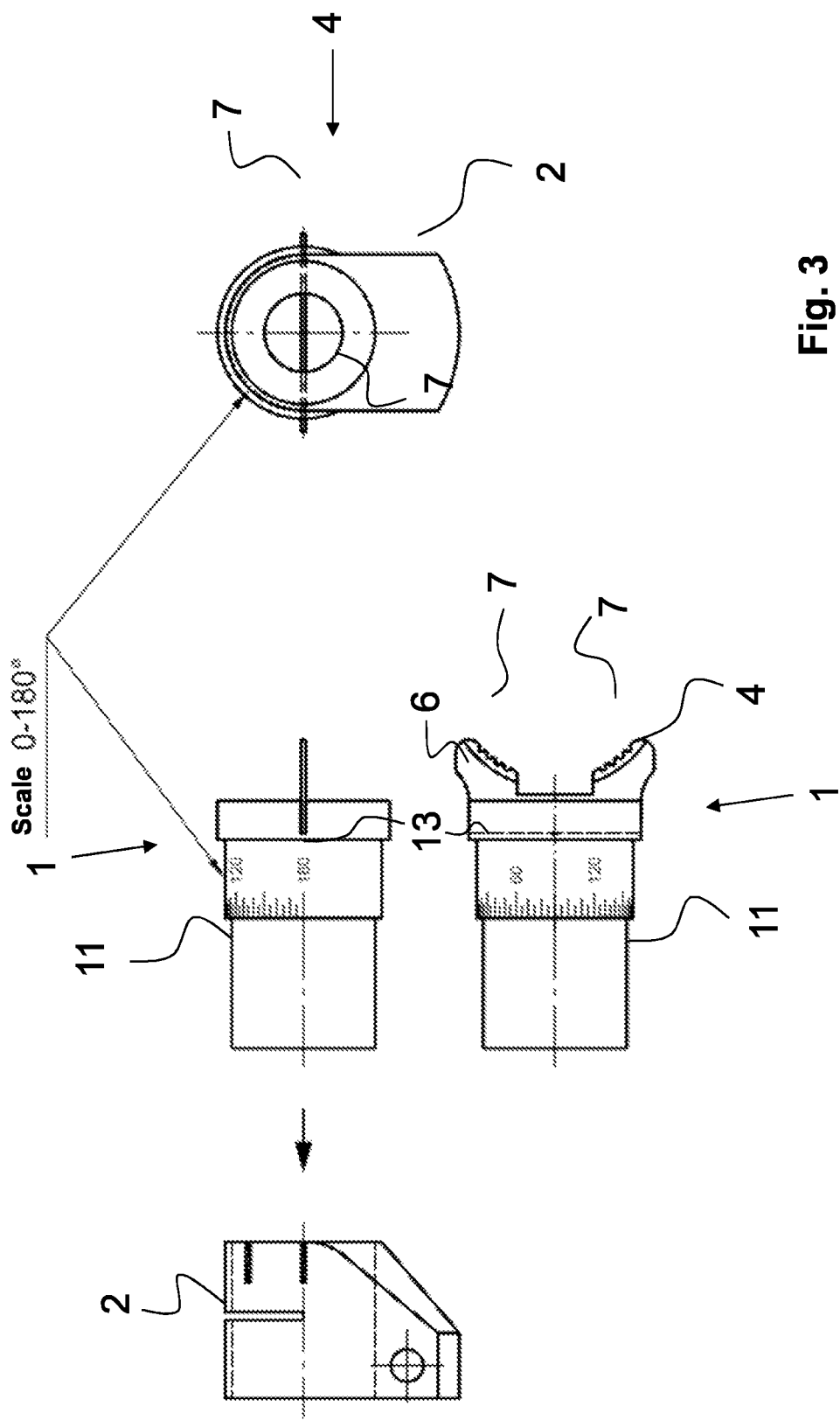
FIG. 3 shows schematic partial views of a further embodiment of a device according to the invention, wherein without the provision of an adapter the marker can be coupled to an integral insertion zone directly to a slit lamp.

FIG. 3 shows a further embodiment of a device according to the invention, namely an embodiment which is modified relative to the device shown in FIGS. 1 and 2 for direct coupling to a slit lamp. More precisely, according to FIG. 3 the so-called cornea marker, i.e. the marking head 1, can be mounted directly on a slit lamp without the interposition of an adapter. More precisely, the marking head 1 comprises an integral insertion zone 11 for direct insertion into the retaining device 2. All further components of the device are provided with the same reference numerals as the embodiment according to the FIGS. 1 and 2, so that further statements with reference to the description of FIGS. 1 and 2 are unnecessary.

Figure 4:
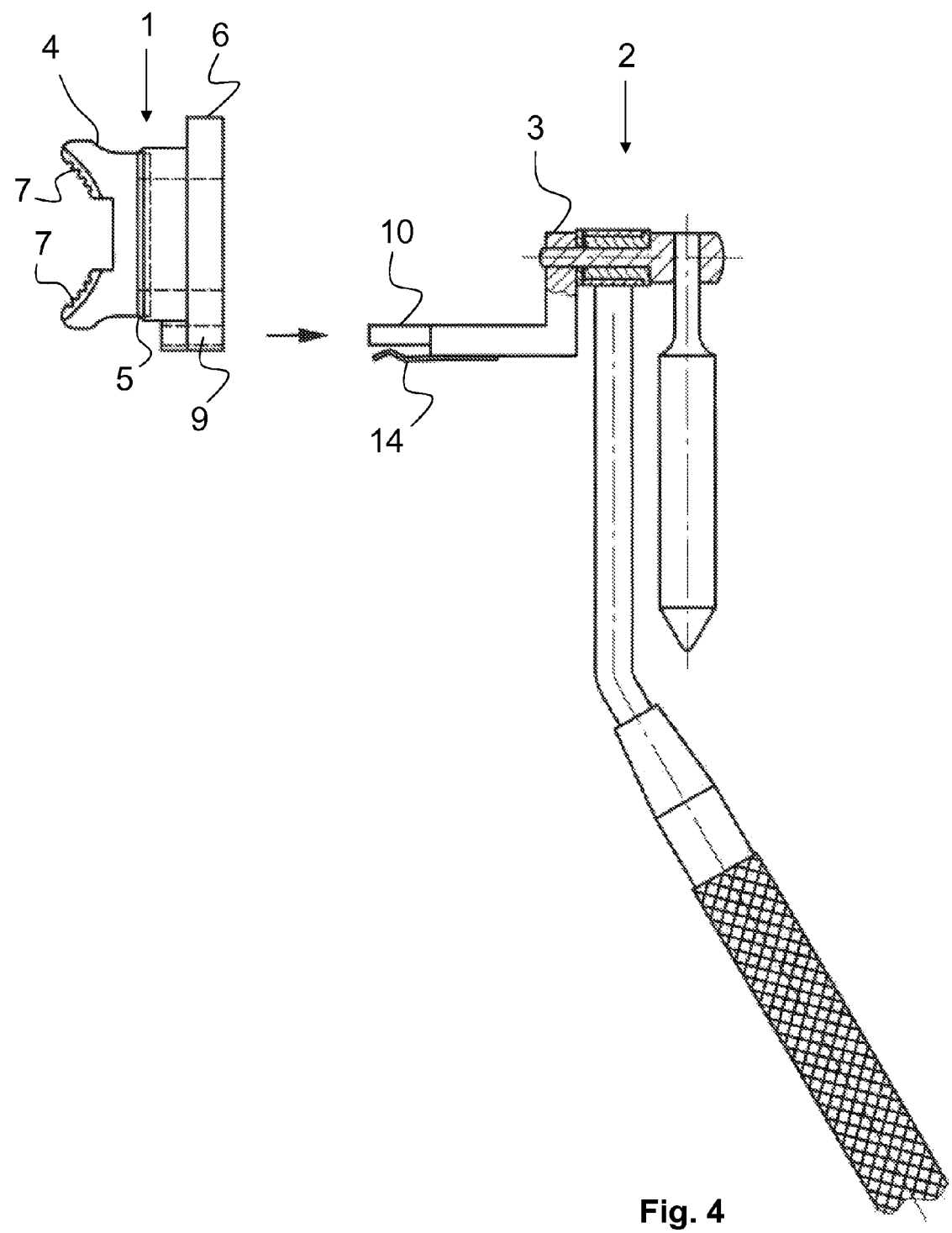
FIG. 4 shows a schematic view of the same marking head as shown in FIG. 1, but for direct coupling to a hand-held instrument for ophthalmological surgery.

FIG. 4 shows a third embodiment of a device according to the invention, wherein the marking head 1 is identical to the marking head 1 shown in FIGS. 1, 2a, 2b and 2c. By means of the receptacle 9 the marking head 1 can be connected directly to the connecting piece 10 of a hand-held instrument, wherein this is any hand-held instrument with an appropriately designed connecting piece 10. In conjunction with the embodiment according to FIGS. 1, 2a, 2b and 2c the versatility of use of the marking head 1 can be seen, wherein a satisfactory coupling between the marking head 1 and any retaining device 2 can be implemented.

In the embodiment shown in FIG. 4 the retaining device 2 is designed as a hand-held ophthalmological instrument with gravity-loaded pendulum mount for the marking head 1.

FIGS. 5a and 5b show the embodiment of FIGS. 4a, 4b in detailed side view, wherein according to FIG. 5a the marking head 1 is uncoupled from the hand-held instrument or from the retaining device 2. FIG. 5b shows the retaining device 2 which is supported by a so-called pendulum marker. A connecting piece 10 which comprises a spring clip 14 for securing is co-ordinated with the retaining device 2 or the pendulum marker. The connecting piece 10 with the spring clip 14 serves for introduction/insertion into a receptacle 9 co-ordinated with the marking head 1.

Figure 6:
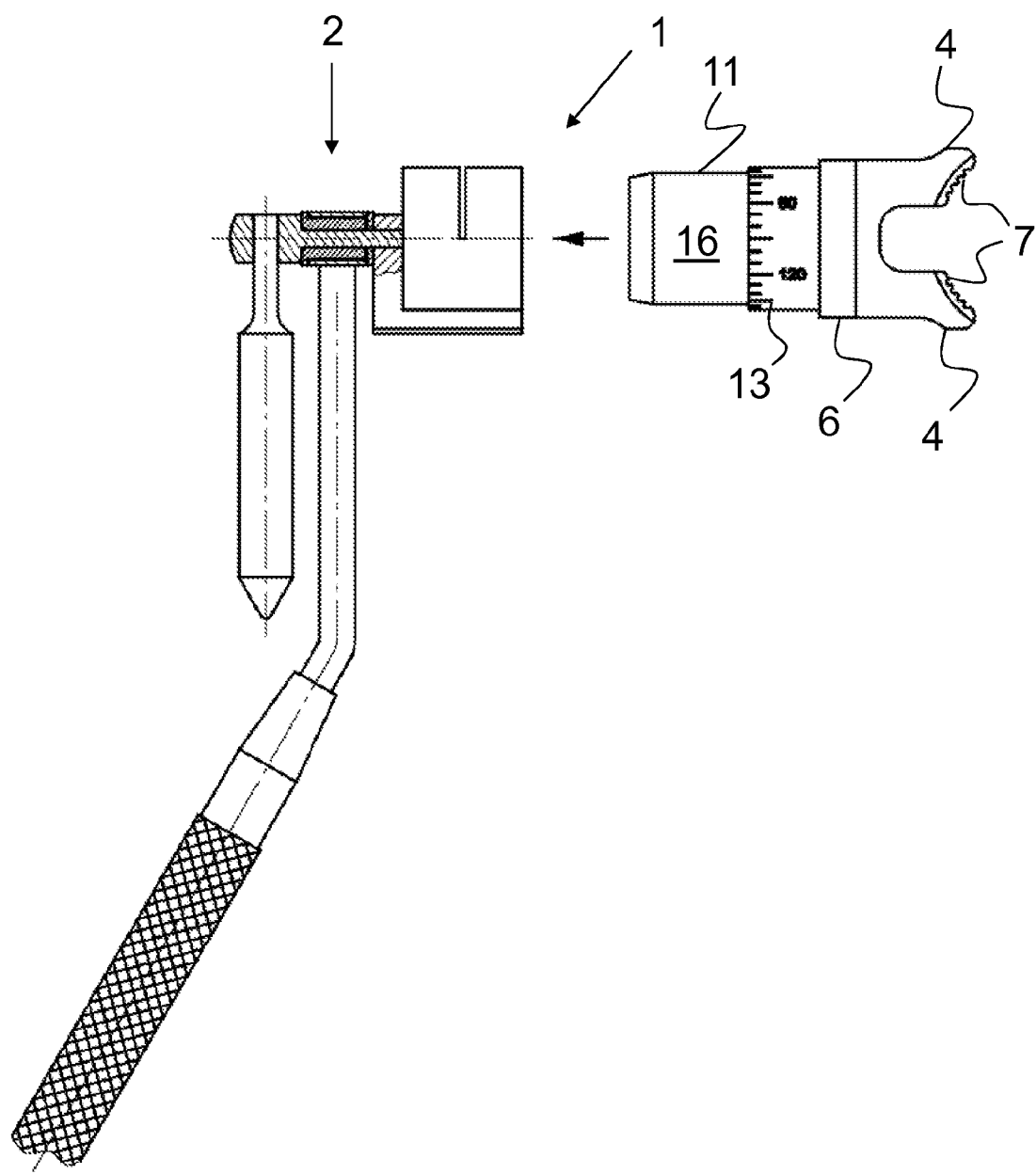
FIG. 6 shows a schematic view of a further embodiment of an ophthalmological hand-held instrument with a marking head which can be coupled to it, wherein the marking head can be fitted directly onto the hand-held instrument.

FIG. 6 shows a further embodiment of a device according to the invention, specifically a so-called pendulum marker. The basic design corresponds to the embodiment of FIGS. 4 and 5. In contrast to the embodiment of FIGS. 4 and 5, the embodiment according to FIG. 6 is equipped with an integral connector 15 which is designed in the manner of a slotted sleeve.

The marking head 1 can be inserted with a connecting piece 16, which comprises an insertion zone 11, into the connector 15 and can be fixed or locked there.

With regard to the connector 15 it may be remarked that the wall thereof is closed in the front region, and is slotted further back, i.e. on the side facing away from the insertion side. The wall acts like a spring, so that by utilising the material-specific tension the connecting piece 16 can be inserted into the connector 15 and can be held there by material tension.

Otherwise the other components of the embodiment shown in FIG. 6 correspond to the components of the embodiment of FIGS. 4 and 5.

Finally it may be remarked that the retaining device may be any equipment in the sense of hand-held instruments or free-standing devices which are suitable for positioning of the marking head relative to the human eye.

The statements above serve only to explain the claimed teaching by way of example, but do not limit the teaching to the two embodiments.

The invention claimed is:

1. A device for applying a marking to the human eye, in particular on the cornea, said device comprising:
    a marking head and a retaining device which supports the marking head,
    wherein a slit lamp or a tonometer, without an actual functional head, serves as the retaining device,
    wherein the marking head comprises a marking element and a support which retains the marking element in a predeterminable or variable angular position, wherein the support is disposed non-rotatably with respect to the retaining device or to a reference line thereof and wherein the marking head is detachable from the retaining device,
    wherein the marking head comprises coupling means for direct connection to the retaining device via insertion of a connection piece,
    wherein the connection piece is co-ordinated with the retaining device, and
    wherein the marking element comprises a marking tool which can be wetted by marking ink for marking a straight line or at least two points or sections of a straight line.

2. The device as claimed in claim 1, wherein the marking tool has two serrated marking flanks which are at least partially bent.

3. The device as claimed in claim 1, wherein the marking element is fastened on or in an inner rotating ring which is rotatable in the support designed as an outer retaining ring by hand or by means of a tool.

4. The device as claimed in claim 3, wherein the inner rotating ring comprises a marker symbolizing the angular position and the outer retaining ring comprises a scale to indicate the angular position, in the range from 0 to 180 degrees.

5. The device as claimed in claim 1, wherein the coupling means and/or the connecting piece comprise a spring-loaded latch for reciprocal latching.

6. The device as claimed in claim 1, wherein the marking head is connected to the slit lamp or tonometer via an adapter comprising a coupling means or a connecting piece.

7. A device for applying a marking to the human eye, in particular on the cornea, said device comprising:
    a marking head and a retaining device which supports the marking head,
    wherein a slit lamp or a tonometer, without an actual functional head, serves as the retaining device,
    wherein the marking head comprises a marking element and a support which retains the marking element in a predeterminable or variable angular position, wherein the support is disposed non-rotatably with respect to the retaining device or to a reference line thereof and wherein the marking head is detachable from the retaining device,
    wherein the marking head comprises coupling means for indirect connection to the retaining device via insertion of a connection piece,
    wherein the connection piece is co-ordinated with an interposed adapter, and
    wherein the marking element comprises a marking tool which can be wetted by marking ink for marking a straight line or at least two points or sections of a straight line.

8. The device as claimed in claim 7, wherein the marking tool has two serrated marking flanks which are at least partially bent.

9. The device as claimed in claim 7, wherein the marking element is fastened on or in an inner rotating ring which is rotatable in the support designed as an outer retaining ring by hand or by means of a tool.

10. The device as claimed in claim 9, wherein the inner rotating ring comprises a marker symbolizing the angular position and the outer retaining ring comprises a scale to indicate the angular position in the range from 0 to 180 degrees.

11. The device as claimed in claim 7, wherein the coupling means and/or the connecting piece comprise a spring-loaded latch for reciprocal latching.

12. The device as claimed in claim 7, wherein the marking head is connected to the slit lamp or tonometer via an adapter comprising a coupling means or a connecting piece.

13. A device for applying a marking to the human eye, in particular on the cornea, said device comprising:
a marking head and a retaining device which supports the marking head,
wherein a slit lamp or a tonometer, without a functional head, serves as the retaining device,
wherein the marking head comprises a marking element and a support which retains the marking element in a predeterminable or variable angular position, wherein the support is disposed non-rotatably with respect to the retaining device or to a reference line and wherein the marking head is detachable from the retaining device
wherein the marking head comprises a connection piece wherein the connection piece comprises an insertion zone for direct coupling to the retaining device via insertion into a connector of the retaining device,
wherein the connector is designed in the manner of a slotted sleeve, and
wherein the marking element comprises a marking tool which can be wetted by marking ink for marking a straight line or at least two points or sections of a straight line.

* * * * *